(12) United States Patent
Lampe et al.

(10) Patent No.: US 11,278,419 B2
(45) Date of Patent: Mar. 22, 2022

(54) EXPANDABLE SUBTALAR JOINT IMPLANT AND INSERTION DEVICE

(71) Applicants: Brandon Lampe, Forney, TX (US); Binoy Sheth, Dallas, TX (US); Thomas Zink, San Antonio, TX (US)

(72) Inventors: Brandon Lampe, Forney, TX (US); Binoy Sheth, Dallas, TX (US); Thomas Zink, San Antonio, TX (US)

( * ) Notice: Subject to any disclaimer, the term of this patent is extended or adjusted under 35 U.S.C. 154(b) by 401 days.

(21) Appl. No.: 16/244,199

(22) Filed: Jan. 10, 2019

(65) Prior Publication Data
US 2019/0209334 A1 Jul. 11, 2019

Related U.S. Application Data

(60) Provisional application No. 62/615,471, filed on Jan. 10, 2018.

(51) Int. Cl.
*A61F 2/42* (2006.01)
*A61F 2/46* (2006.01)
*A61F 2/30* (2006.01)

(52) U.S. Cl.
CPC ........ *A61F 2/4202* (2013.01); *A61F 2/30771* (2013.01); *A61F 2/4606* (2013.01); *A61F 2/4603* (2013.01); *A61F 2002/30143* (2013.01); *A61F 2002/30405* (2013.01); *A61F 2002/30579* (2013.01); *A61F 2002/30851* (2013.01); *A61F 2002/4207* (2013.01); *A61F 2002/4223* (2013.01); *A61F 2002/4629* (2013.01)

(58) Field of Classification Search
CPC .................. A61F 2/402; A61F 2002/4207
See application file for complete search history.

(56) References Cited

U.S. PATENT DOCUMENTS

| | | | |
|---|---|---|---|
| 2011/0166608 A1* | 7/2011 | Duggal | A61B 17/7233 606/320 |
| 2017/0065423 A1* | 3/2017 | Lauf | A61B 17/68 |
| 2017/0303938 A1* | 10/2017 | Rindal | A61B 17/864 |

* cited by examiner

*Primary Examiner* — Jason-Dennis N Stewart
(74) *Attorney, Agent, or Firm* — Brennan, Manna & Diamond, LLC

(57) ABSTRACT

A subtalar implant that can be expanded/contracted in vivo to adjust the amount of distraction applied to the subtalar joint of a patient and a related insertion device are disclosed herein. More specifically, the subtalar implant can expand both radially and also in the angle between the proximal and distal end of the outer component of the implant. The implant comprises an internal component that allows for the distal or proximal ends of the implant to be manipulated via the insertion device. The subtalar implant and the related insertion device permit a surgeon to adjust the implant construct to suit a particular patient.

16 Claims, 3 Drawing Sheets

EXPANDABLE SUBTALAR JOINT IMPLANT AND INSERTION DEVICE

CROSS-REFERENCE TO RELATED APPLICATION

This application claims priority from Provisional Patent Application Ser. No. 62/615,471 filed on Jan. 10, 2018.

FIELD OF THE INVENTION

The present invention relates generally to a subtalar implant for stabilizing the subtalar joint in the human foot, and a related insertion device for installing and manipulating the subtalar implant in vivo. More specifically, the subtalar implant is designed to expand in vivo to adjust the amount of distraction applied to the subtalar joint by the implant and reduce the likelihood that a second procedure, and the risks associated therewith, will be required.

BACKGROUND

The subtalar joint, also known as the talocalcaneal joint, is a compound joint positioned directly below the ankle joint. It is comprised of the calcaneus or heel bone and a column-shaped bone called the talus. The subtalar joint is an important component of an individual's ability to move as it helps to readjust the lateral position of the foot as an individual navigates over uneven or shifting terrain. Absent the subtalar joint, it would be very difficult for an individual to move, run, jump, or walk with any precision or accuracy.

The subtalar joint is also multi-articular, meaning that it is capable of moving in more than one direction. More specifically, there are three articulated facets of the subtalar joint which allow it to move forward (i.e., anterior articulation), backward (i.e., posterior articulation), and laterally. The facets are generally known as the anterior subtalar joint (ASTJ), the medial subtalar joint (MSLJ), and the posterior subtalar joint (PSTJ). Further, the various bones comprising the joint are held in placed by strong but flexible ligaments. The main ligament is referred to as the interosseous talocalcaneal ligament, and it runs along a groove between the bones called the tarsal channel. Four other weaker ligaments provide the subtalar joint with added stability. A tissue called the synovial membrane is also positioned between the calcaneus and talus, and helps to lubricate the subtalar joint space.

Unfortunately, because the subtalar joint is so crucial to an individual's mobility, it is also vulnerable to wear-and-tear, trauma (e.g., from high-impact activities), and other joint-specific disorders. Damage to the subtalar joint can be difficult to detect or pinpoint without imaging tests, such as ultrasound, MRI and the like. Further, any damage done to the subtalar joint, including any connective tissues that support it, can trigger pain, lead to foot deformity (temporary and permanent), and affect an individuals' gait and mobility. This damage may be generally categorized as either capsular or non-capsular.

More specifically, capsular disorders are those in which the subtalar joint is primarily involved, and intrinsically impairs how the joint is meant to function. Capsular disorders may include, but are not limited to: (a) gout, which is a type of arthritis that commonly affects the first metatarsophalangeal joint, but can also cause inflammation and pain in the subtalar joint; (b) rheumatoid arthritis, which is an autoimmune form of arthritis in which the body's immune system primarily attacks joint tissues such as those of the ankle and/or foot; (c) osteoarthritis, which is a wear-and-tear form of arthritis that is often caused by a previous joint injury, such as a fracture; and (d) juvenile idiolathic arthritis, which is a type of pediatric arthritis that commonly affects the subtalar joint.

In comparison, non-capsular disorders are those disorders in which the subtalar joint is indirectly affected by defects and/or injuries of the foot and/or ankle. Non-capsular disorders may include, but are not limited to: (a) subtalar dislocation or "basketball foot," which typically occurs if an individual lands too hard on the inside or outside of his or her foot; (b) subtalar instability, which is a lateral weakness in the joint that can cause the ankle to suddenly "give way" or buckle and can lead to the twisting of the ankle or chronic inflammation due to extreme pressure being placed on the lateral ligament; (c) pes planus or "flat feet," which is a collapsed arch in the foot that typically, develops during childhood and can oftentimes cause extreme pain if the foot is not structurally supported; (d) pes cavus or a "high instep", which refers to an exaggerated arch of the foot that is often caused by a neurological disorder that alters its structure and can lead to a severe restriction of movement, pain, and disability; (e) polyarthropathy, which is a condition in which pain and inflammation occur in multiple joints including the subtalar joint; and (f) tarsal coalition, which is a fusion of the bones in the hindfoot and is characterized by a limited range of motion, pain, and a rigid, flat foot.

Further, many of the above referenced afflictions and/or disorders can be further delineated into subcategories. For example, flexible flatfoot is one of the most common types of flatfoot or pes planus, and can be anatomically described as excessive pronation during weight bearing due to anterior and medial displacement of the talus. Generally stated, the term flexible means that the foot is flat when the individual is standing or the foot is weight-bearing, and the arch returns to the foot when the individual is not standing or no longer bearing weight. Flexible flat foot may be congenital in nature, or may be acquired in adulthood due to posterior tibial tendon dysfunction.

Conservative treatment methods for treating flatfoot include orthotics or shoe modifications, stretching exercises and medication. Various surgical techniques of subtalar arthroereisis have also been used in the treatment of patients who have failed conservative treatment. Arthroereisis is the limitation of excessive movement across the joint. More specifically, subtalar arthroereisis is designed to correct the excessive talar displacement and calcaneal eversion by placing an implant in the sinus tarsi, the canal located between the talus and the calcaneus. By inserting an implant in the subtalar joint, eversion of the hindfoot can be controlled. Subtalar arthroereisis is often combined with other procedures, including, but not limited to: tendon transfers, tendon reconstructions, and osteotomies.

Unfortunately, current subtalar implants are static designs and are not adjustable in vivo. More specifically, the implants are formed in one piece and typically have a continuous channel throughout. The implant also comprises a fixed conical sleeve contour which comprises a thread on the lateral surface to anchor the implant in the calcaneus and in the talus. Thus, the implants are threaded into the subtalar joint, but the size of the resulting distraction is limited to the size of the implant, and cannot be increased or radially adjusted. This inflexibility in the design requires the subtalar joint implants to be provided to the surgeon in several shapes and sizes, who then must choose a suitable subtalar implant during the operation to get the correct fit in the patient's subtalar joint. If the selected implant does not fit optimally;

the surgeon then must remove the implant (perhaps in a second procedure) and replace it with a more suitable subtalar implant, thereby potentially exposing the patient to additional surgeries and the various risks attendant thereto.

Consequently, there is a long felt need in the art for an adjustable subtalar joint implant that reduces the number of implants that must be provided to a surgeon to choose from in a surgical setting. There also exists in the art a long felt need for a subtalar joint implant that can be adjusted both radially and angularly in vivo, thereby reducing the likelihood of the patient having to undergo additional surgeries and the risks attendant thereto to insure an optimal fit. Finally, a long felt need exists in the art for an insertion device that enables the surgeon to install and manipulate the size, shape and orientation of the implant device in the subtalar joint in vivo.

More specifically, the present invention discloses a subtalar implant that can be expanded in vivo to adjust the amount of distraction applied to the patient's subtalar joint. The implant of the present invention can expand both radially and also in the angle between the proximal and distal end of the implant. The implant of the present invention further comprises an internal component that allows for the distal or proximal ends of the implant to be manipulated in vivo. This allows the surgeon to adjust the construct to fit the patient's anatomy and desired final construct fit at the time of the initial implantation, thereby eliminating the possible need for a second procedure and the various risks associated therewith. An insertion device for installing and manipulating the implant device in the subtalar joint in vivo is also disclosed. While this specification makes specific reference to the implant device of the present invention as a way in which to treat flat feet, it will be appreciated by those of ordinary skill in the art that aspects of the present invention are also equally amenable to other like applications and other subtalar joint afflictions and/or disorders.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, comprises a subtalar implant comprising an outer component and an inner component that are capable of moving independently of one another. The outer component is generally conical in shape and comprises a threaded interior section, a proximal end and a distal end. The outer surface of the inner component is also threaded to matingly engage the threaded interior section of the outer component, thereby causing the proximal end of the outer component to expand both radially and angularly relative to its distal end. The inner component may further be cannulated to permit the use of a guide wire during implantation or otherwise.

In an alternative embodiment, the present invention may comprise both the subtalar implant described above and an insertion device having a first end with a handle located thereon, an elongated body portion and an opposing second end that can operatively attach to said subtalar implant and be used to securely install and manipulate the subtalar implant into a subtalar joint of a patient in vivo. More specifically, the second end of said insertion device is configured to permit the proximal end of the outer component of the subtalar implant to expand, both radially and angularly relative to its distal end, while remaining attached to the inserter. This allows a user to keep the subtalar implant in place in vivo while the outer component of the subtalar implant is expanded.

In yet a further alternative embodiment of the present invention, the insertion device may further comprise an inner part threading instrument that extends through a longitudinal opening in the insertion device and enables the user to manipulate (i.e., thread or unthread) the inner component of the subtalar implant relative to the outer component in vivo. More specifically, the inner part threading instrument of the insertion device is configured to permit the proximal end of the outer component of the subtalar implant to expand, both radially and angularly relative to its distal end, while remaining attached to the insertion device. This allows a user to keep the subtalar implant in place in vivo while the outer component of the subtalar implant is expanded.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

DETAILED DESCRIPTION

Figure 1A:
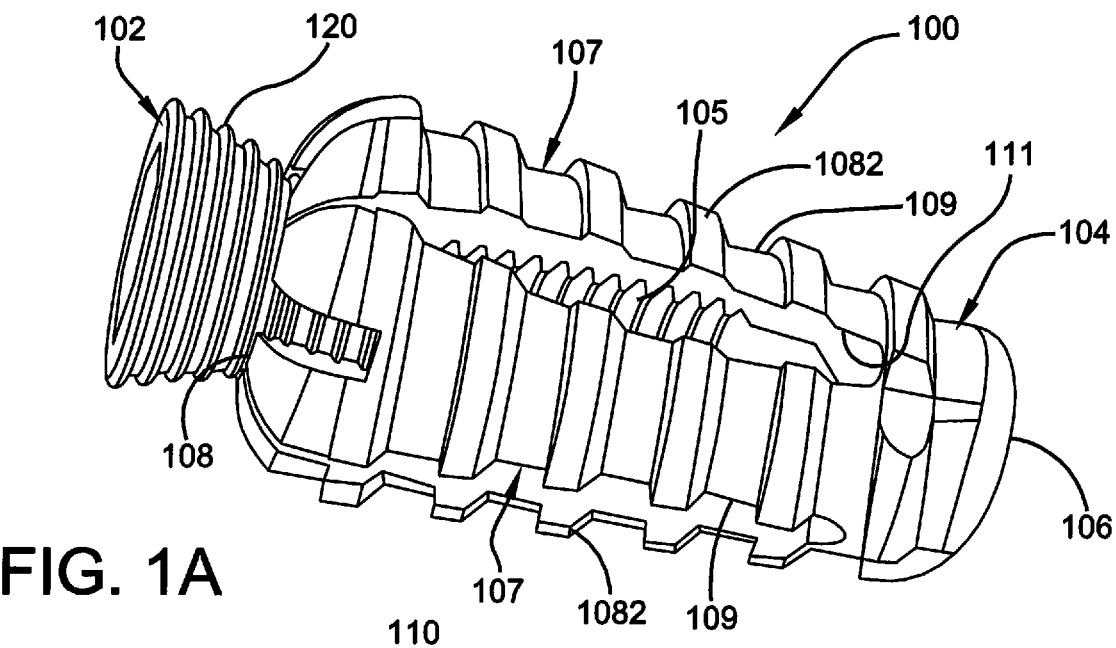
FIG. 1A illustrates a perspective view of the subtalar implant in accordance with the disclosed architecture and with the outer component in a generally retracted or closed position.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

Generally stated, and in one embodiment thereof, the present invention discloses a subtalar implant that can be expanded in vivo to adjust the amount of distraction applied to the subtalar joint of a patient. More specifically, the proximal end of the outer component of the subtalar implant can expand or contract both radially and also in the angle between the proximal and distal end of the outer component of the subtalar implant. The subtalar implant further comprises an internal component that enables the user or surgeon to securely install the subtalar implant in a patient, and to manipulate the size, shape and orientation of the same in vivo. In this manner, the surgeon is able to adjust the construct of the subtalar implant to more closely fit the patient's anatomy and to achieve the desired final construct fit without the need for a second surgical procedure and the risks associated therewith.

In an alternative embodiment, the present invention may comprise both the subtalar implant described above and an insertion device having a first end with a handle located thereon, an elongated body portion and an opposing second end that can operatively attach to said subtalar implant and be used to securely install and manipulate the subtalar implant into a subtalar joint of a patient in vivo. More specifically, the second end of said insertion device is configured to permit the proximal end of the outer component of the subtalar implant to expand, both radially and angularly relative to its distal end, while remaining attached to the insertion device. This allows the surgeon to keep the subtalar implant in place in vivo while the implant is expanded or manipulated.

In yet a further alternative embodiment of the present invention, the insertion device may further comprise an inner part threading instrument that extends through a longitudinal opening in the insertion device and enables the surgeon to manipulate (i.e., thread or unthread) the inner component of the subtalar implant relative to the proximal end of the outer component in vivo.

Referring initially to the drawings, FIG. 1A illustrates a subtalar implant 100 comprising an inner component 102 and an outer component 104 with the outer component 104 in a generally retracted or closed position. Both the inner component 102 and the outer component 104 may be manufactured using additive manufacturing (AM) techniques and constructed as one part, provided that inner and outer components 102, 104 are capable of moving independently of one another, Further, the components 102 and 104 can be manufactured using a combination of other molding or machining techniques (injection molding, machining, etc.) to produce the subject subtalar implant components. These additional techniques include, without limitation, material extrusion, vat photo polymerization, powder bed fusion, material jetting, binder jetting, sheet lamination and directed energy deposition. Notwithstanding, subtalar implant components 102 and 104 are preferably manufactured from titanium, specifically Ti 6 Al 4 V-ELI, though the same can be manufactured from any other suitable medical grade material as is known in the art.

Additionally, the subtalar implant 100 and its components can be any suitable size, shape, and configuration as is known in the art without affecting the overall concept of the invention. One of ordinary skill in the art will appreciate that the shape and size of the subtalar implant 100 as shown in the FIGS. is for illustrative purposes only and many other shapes and sizes of the implant 100 are well within the scope of the present disclosure. Although dimensions of the implant 100 (i.e., length, width, and height) are important design parameters for good performance, the subtalar implant 100 may be any shape, size or configuration that ensures optimal performance during use.

Outer component 104 is preferably comprised of a threaded interior portion 105, a distal end 106, a plurality of repositionable finger portions 107 that extend outwardly from said distal end 106 in the direction of a proximal end 108 of outer component 104. Further, outer component 104 is preferably generally conical in shape such that the distal end 106 is smaller in diameter than the proximal end 108 of the outer component 104 of the subtalar implant 100. Notwithstanding, outer component 104 can take the form of any other suitable shape as is known in the art without affecting the overall concept of the present invention, provided that it is capable of expanding/contracting in vivo.

Figure 1B:
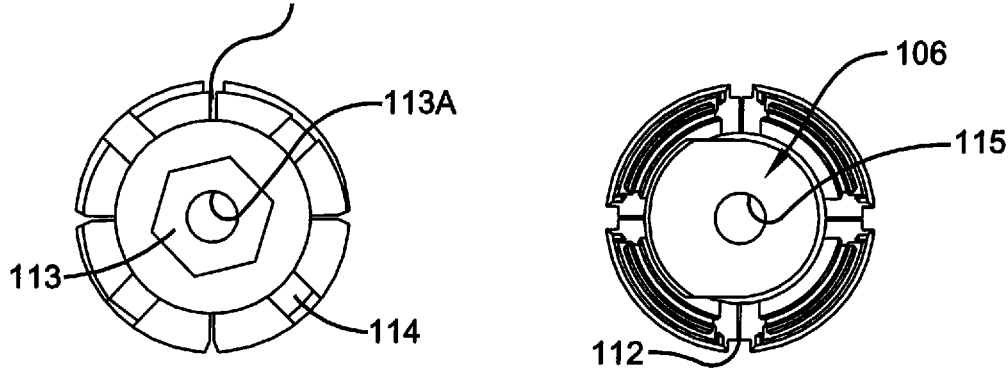
FIG. 1B illustrates a perspective view of the proximal end of the subtalar implant of FIG. 1A in accordance with the disclosed architecture.
Figure 1C:
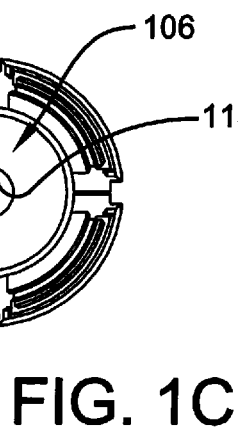
FIG. 1C illustrates a perspective view of the distal end of the subtalar implant of FIG. 1A in accordance with the disclosed architecture.

Additionally, as shown in FIGS. 1A-C, the distal end 106 of outer component 104 is preferably rounded or chamfered for relatively easy insertion into the subtalar joint of a patient (not shown), and also comprises a plurality of protrusions or cuts 112 which act to cut threads into the patient's bone to further secure the subtalar implant 100 within the subtalar joint (not shown). As best shown in FIG. 1C, distal end 106 of subtalar implant 100 may further comprise an opening 115 therein for access by, for example, a guidewire or other instrumentation.

As best shown in FIG. 1A, repositionable finger portions 107 may further comprise alternating ridges 1082 and valleys 109 for further engagement of a patient's bone upon installation in the subtalar joint of a patient. Further, the proximal end 108 of outer component 104 also comprises a plurality of cuts 110 that allow the repositionable finger portions 107 of outer component 104 to expand and retract and to move independently of one another at the proximal end 108 of outer component 104 as inner component 102 is threaded in and out of the proximal end 108 of outer component 104, as described more fully below.

As also shown in FIG. 1A, longitudinal openings or channels 111 may be positioned between adjacent repositionable finger portions 107 to further facilitate the independent movement of said finger portions 107. Additionally, proximal end 108 of outer component 104 may further comprise a plurality of blind cuts 114 that are positioned to further accept the end of an insertion device (not shown), as explained more fully below.

Figure 2:
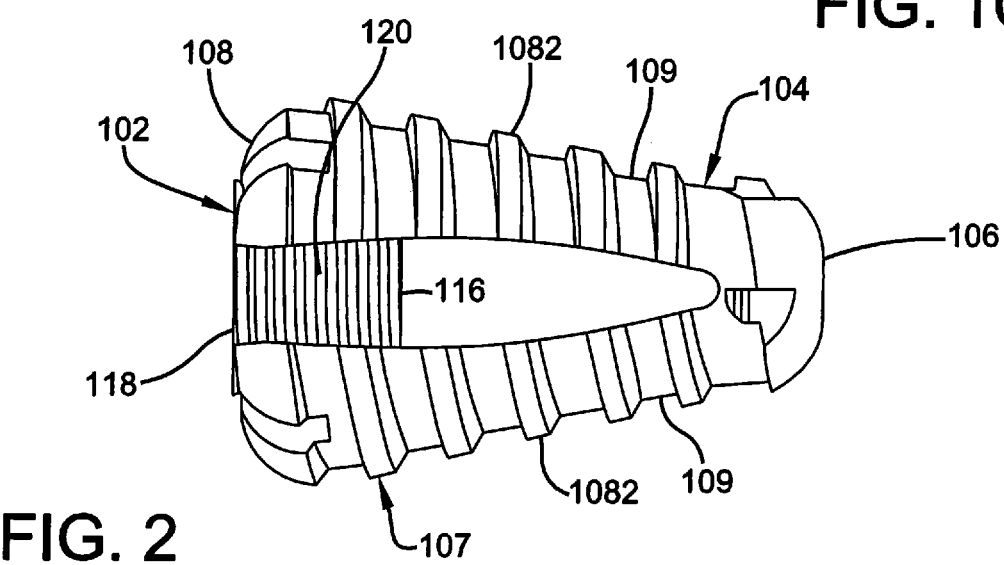
FIG. 2 illustrates a perspective view of the subtalar implant in accordance with the disclosed architecture and with the proximal end of the outer component in a generally expanded position, both radially and angularly relative to the distal end of the outer component.

As best shown in FIGS. 1A and 2, inner component 102 is also comprised of a threaded outer surface 120, a distal end 116 and a proximal end 118. Inner component 102 is preferably generally conical in shape such that the distal end 116 is smaller in diameter than the proximal end 118 of the inner component 102. Threaded outer surface 120 is sized, shaped and pitched to engage the plurality of cuts 110 and internal threads 105 of outer component 104, such that proximal end 108 of the outer component 104 will have the ability to expand when the inner component 102 is threaded into the proximal end 108 of outer component 104 as shown in FIG. 2, and retract when inner component 102 is unthreaded from the proximal end 108 of outer component 104, as shown in FIG. 1A. More specifically and as shown in FIG. 2, the subtalar implant 100 expands both radially and also in the angle between the proximal 108 and distal 106 end of the subtalar implant 100.

As best shown in FIG. 1B, proximal end 118 of inner component 102 further comprises a first opening 113 for receipt of a portion of an insertion device 300 as described more fully below. First opening 113 is preferably hexagonal in shape to ensure a secure fit with a portion of the insertion device 300, though other geometric shapes may also be used provided that they correspond to the shape and size of the end of the insertion device 300, namely tip 502 as discussed more fully below. As best shown in FIG. 1B, first opening 113 preferably also comprises a smaller second continuous opening 113A therein for access by, for example, a guidewire or other instrumentation. In fact, the entire subtalar implant 100 is preferably cannulated to allow for the insertion of a guide wire (not shown), which can be used during implantation of implant 100 into a patient (not shown) or for other purposes.

Figure 3:
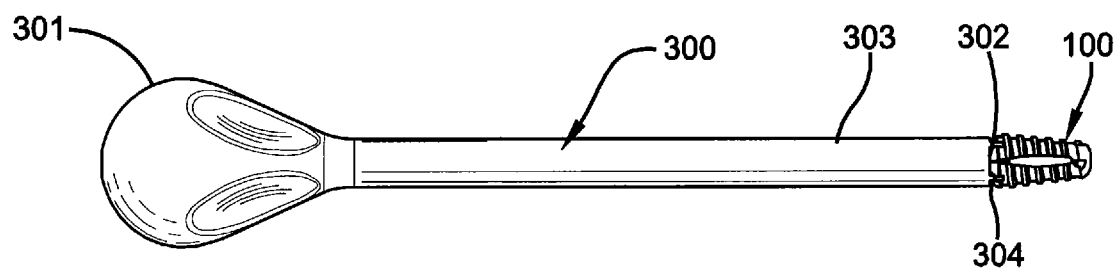
FIG. 3 illustrates a perspective view of the subtalar implant movably connected to an insertion device in accordance with the disclosed architecture.
Figure 4:
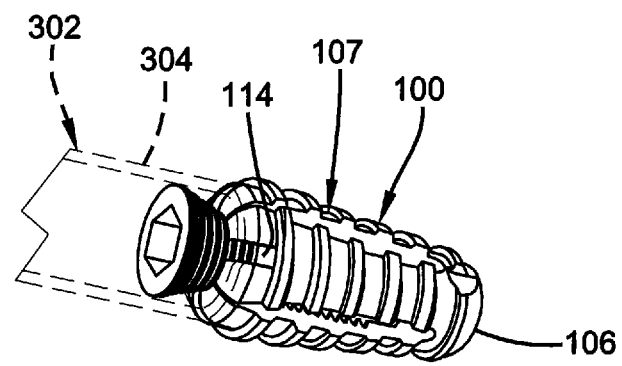
FIG. 4 illustrates a perspective view of the subtalar implant movably connected to an end of an insertion device in accordance with the disclosed architecture.
Figure 5:
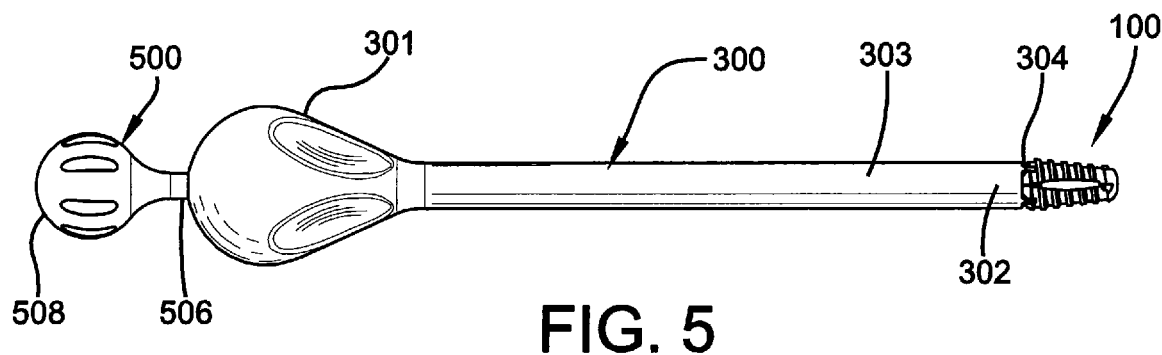
FIG. 5 illustrates a perspective view of the subtalar implant and insertion device of FIG. 3 further comprising an inner part threading instrument for threading the inner component of the subtalar implant into the outer component in accordance with the disclosed architecture.

Typically, as shown in FIGS. 3-4, the subtalar implant device 100 is removably secured to a generally rod-shaped insertion device 300. Insertion device 300 is preferably comprised of first end 301, a second or inserter end 302, and an elongated body member 303 positioned therebetween. First end 301 may be comprised in the shape of a handle, as best shown in FIG. 3, for easily manipulation/rotation of inserter 300. The inserter end 302 engages the proximal end 108 of the outer component 104. More specifically and as best shown in FIGS. 4 and 5, inserter end 302 of insertion device 300 preferably comprises one or more inserter prongs 304 that removably secure to one or more of the plurality of blind cuts 114 in the proximal end 108 of the outer component 104. Thus, the insertion device 300 allows for the proximal end 108 of the outer component 104 of subtalar implant 100 to expand and/or for the angle of the proximal end 108 relative to the distal end 106 to increase while still being connected to the insertion device 300. This allows the user to keep the subtalar implant 100 in place while finger portions 107 of the outer component 104 are expanded. Likewise, the inserter prongs 304 can also continue to be removably attached to one or more of the plurality of blind cuts 114 of the outer component 104 while inner component 102 is being unthreaded from the proximal end 108 of outer component 104, thereby causing the finger portions 107 to retract or close as best shown in FIG. 1A.

Figure 6:
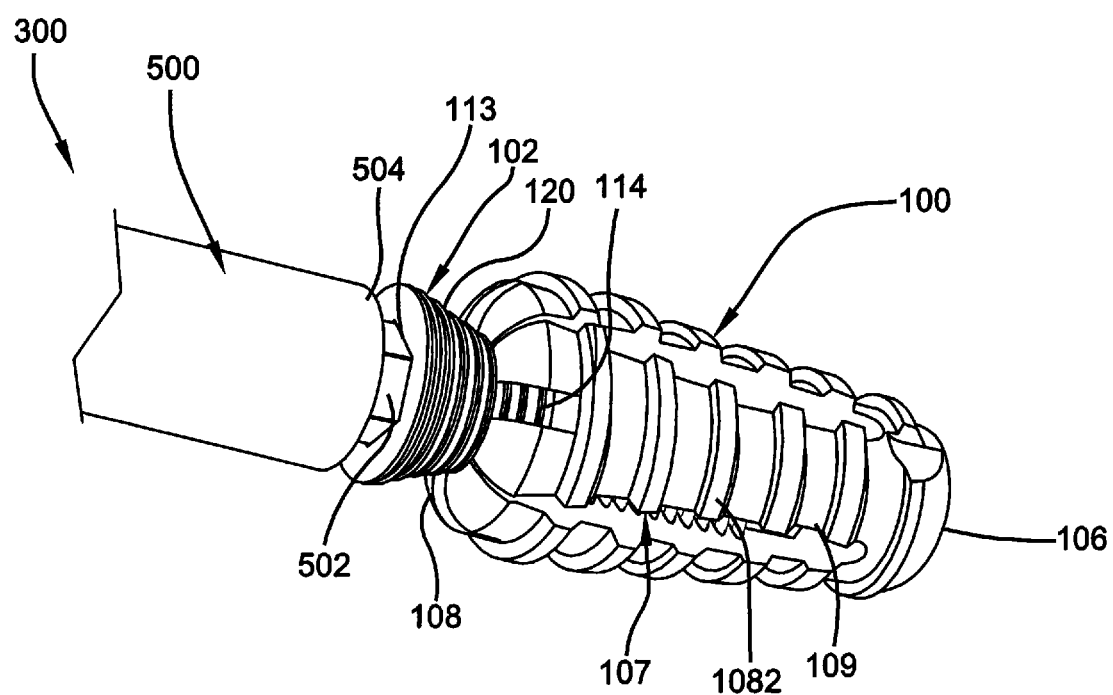
FIG. 6 illustrates a perspective view of the subtalar implant threaded to an end of the inner part threading instrument of the insertion device of FIG. 5 in accordance with the disclosed architecture.

As best shown in FIGS. 5-6, the insertion device 300 is preferably cannulated and comprises an inner part threading component 500 which is inserted into the cannulated inserter 300. The inner part threading component 500 is preferably generally rod shaped and comprised of a distal end 504 and a proximal end 506. As best shown in FIG. 5, a handle 508 may be positioned at proximal end 506 for easy manipulation/rotation of inner part threading component 500, as explained more fully below. Distal end 504 of inner part threading component 500 is preferably comprised of a generally hexagon shaped tip 502 for mating engagement with first opening 113 (see FIG. 1B) of the inner component 102, and allows the inner part threading component 500 to thread the inner component 102 into the proximal end 108 of the outer component 104, thereby expanding the finger portions 107 radially and also in the angle between the proximal 108 and distal 106 ends of the outer component 104 of subtalar implant 100. As previously stated, tip 502 doesn't have to be hexagonal in shape and can be any other shape, size or configuration that is known in the art, provided that tip 502 corresponds to the shape, size and configuration of first opening 113.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A subtalar implant comprising:
an inner component conical in shape and comprising a pitched threaded outer surface narrowing from a proximal end to a distal end, and a guidewire opening; and
an outer component comprising a proximal end comprising an opening for a guidewire and a plurality of blind cuts configured to aid in insertion of the subtalar implant, a distal end, a plurality of finger portions configured to move independently, and a plurality of longitudinal channels positioned between adjacent finger portions.

2. The subtalar implant of claim 1, wherein the plurality of finger portions are repositionable by threading the inner component into the outer component.

3. The subtalar implant of claim 1, wherein each of the plurality of finger portions further comprises at least one ridge and one valley.

4. The subtalar implant of claim 1, wherein the inner component is removably attached to the proximal end of the outer component.

5. The subtalar implant of claim 1, wherein the outer component is further comprised of a conical shape and a threaded interior portion.

6. The subtalar implant of claim 1, wherein the distal end of the outer component is comprised of a rounded surface, a plurality of cuts and an opening.

7. The subtalar implant of claim 1, wherein the proximal end of the outer component expands radially and angularly in relation to the distal end when said inner component is installed in the proximal end of said outer component.

8. The subtalar implant of claim 1, wherein the outer component is comprised of a plurality of outer cuts.

9. A subtalar implant system comprising:
a subtalar implant comprising an inner component conical in shape comprising a pitched threaded outer surface narrowing from a proximal end to a distal end, and a guidewire opening; and an outer component comprising a proximal end comprising an opening for a guidewire and a plurality of blind cuts configured to aid in insertion of the subtalar implant, a distal end, a plurality of finger portions configured to move independently, and a plurality of longitudinal channels positioned between adjacent finger portions; and
an inserter device.

10. The subtalar implant system of claim 9, wherein the inserted device comprises at least one inserter prong for engaging the proximal end of the outer component.

11. The subtalar implant system of claim 9, wherein the inserted device further comprises a threading component comprised of a tip for engaging the inner component of the subtalar implant.

12. The subtalar implant system of claim 11, wherein at least a portion of the threading component is positioned within an opening in the inserter device.

13. The subtalar implant system of claim 11, wherein the outer component expands radially and angularly in relation to the distal end when the tip engages the inner component and the inner component is rotated.

14. A subtalar implant system comprising:
  a subtalar implant comprising an inner component conical in shape comprising a pitched threaded outer surface narrowing from a proximal end to a distal end, and a guidewire opening; and an outer component comprising a proximal end comprising an opening for a guidewire and a plurality of blind cuts configured to aid in insertion of the subtalar implant, a distal end, a plurality of finger portions configured to move independently, and a plurality of longitudinal channels positioned between adjacent finger portions; and
  an inserter device comprised of at least one inserter prong for engaging the plurality of blind cuts of the outer component and a threading component for engaging the inner component, and wherein the inserter device is canulated.

15. The subtalar implant system of claim 14, wherein the outer component expands radially when the threaded component engages the inner component and the inner component is rotated.

16. The subtalar implant system of claim 14, wherein each of the outer component and the inner component are comprised of a conical shape.

\* \* \* \* \*